United States Patent [19]

Henning et al.

[11] Patent Number: 4,977,260
[45] Date of Patent: Dec. 11, 1990

[54] INTERMEDIATES FOR PREPARING MONO-, BI- AND TRICYCLIC AMINO ACIDS

[75] Inventors: Rainer Henning, Hattersheim am Main; Hansjörg Urbach, Kronberg/Taunus, both of Fed. Rep. of Germany

[73] Assignee: Hoechst Aktiengesellschaft, Frankfurt am Main, Fed. Rep. of Germany

[21] Appl. No.: 335,443

[22] Filed: Apr. 10, 1989

Related U.S. Application Data

[62] Division of Ser. No. 122,380, Nov. 19, 1987, Pat. No. 4,849,524.

[30] Foreign Application Priority Data

Nov. 21, 1986 [DE] Fed. Rep. of Germany ....... 3639879

[51] Int. Cl.$^5$ .................. C07D 413/04; C07D 265/02
[52] U.S. Cl. ........................ 544/73; 544/63; 544/71; 544/72
[58] Field of Search ................. 544/63, 71, 72, 73

[56] References Cited

U.S. PATENT DOCUMENTS

| | | | |
|---|---|---|---|
| 4,374,847 | 2/1983 | Gruenfeld | 424/274 |
| 4,508,729 | 4/1985 | Vincent et al. | 514/419 |
| 4,525,301 | 6/1985 | Henning et al. | 260/112.5 R |
| 4,558,064 | 12/1985 | Teetz et al. | 209/96 |
| 4,558,065 | 12/1985 | Urbach et al. | 514/412 |
| 4,562,202 | 12/1985 | Urbach et al. | 514/423 |
| 4,587,258 | 5/1986 | Gold et al. | 514/412 |
| 4,591,598 | 5/1986 | Urbach et al. | 514/412 |
| 4,614,805 | 9/1986 | Urbach et al. | 548/427 |
| 4,620,012 | 10/1986 | Henning et al. | 548/411 |
| 4,659,838 | 4/1987 | Lerch | 548/452 |
| 4,668,796 | 5/1987 | Geiger et al. | 548/452 |
| 4,668,797 | 5/1987 | Urbach et al. | 548/452 |
| 4,684,662 | 8/1987 | Henning et al. | 548/452 |
| 4,691,022 | 9/1987 | Henning et al. | 548/408 |
| 4,714,708 | 12/1987 | Urbach et al. | 514/412 |
| 4,727,160 | 2/1988 | Teetz et al. | 548/452 |
| 4,808,573 | 2/1989 | Gold et al. | 514/19 |
| 4,818,749 | 4/1989 | Gold et al. | 514/19 |
| 4,822,894 | 4/1989 | Geiger et al. | 548/452 |
| 4,831,157 | 5/1989 | Gold et al. | 548/452 |
| 4,868,307 | 9/1989 | Barton et al. | 546/256 |
| 4,886,827 | 12/1989 | Urbach et al. | 514/412 |

FOREIGN PATENT DOCUMENTS

| | | |
|---|---|---|
| 0012401 | 6/1980 | European Pat. Off. . |
| 0012845 | 7/1980 | European Pat. Off. . |
| 0018549 | 11/1980 | European Pat. Off. . |
| 0037231A2 | 10/1981 | European Pat. Off. . |
| 0046953 | 3/1982 | European Pat. Off. . |
| 0049658 | 4/1982 | European Pat. Off. . |
| 0050800 | 5/1982 | European Pat. Off. . |
| 0050850A1 | 5/1982 | European Pat. Off. . |
| 0079022 | 5/1983 | European Pat. Off. . |
| 0090362 | 10/1983 | European Pat. Off. . |
| 3322530 | 1/1985 | Fed. Rep. of Germany . |
| 812859 | 3/1982 | Finland . |
| 813034 | 4/1982 | Finland . |
| 813283 | 4/1982 | Finland . |
| 813422 | 5/1982 | Finland . |
| 2491469 | 5/1983 | France . |
| 64085 | 10/1981 | Israel . |
| 77672 | 5/1982 | Japan . |
| 91974 | 6/1982 | Japan . |
| 112359 | 7/1982 | Japan . |
| 198535 | 9/1984 | New Zealand . |
| 198702 | 8/1985 | New Zealand . |
| 81/5988 | 8/1982 | South Africa . |
| 83/2229 | 10/1983 | South Africa . |
| 519418 | 10/1976 | U.S.S.R. . |
| 2086390 | 5/1982 | United Kingdom . |
| 2095682 | 10/1982 | United Kingdom . |

OTHER PUBLICATIONS

Nakanishi et al., Chemical Abstracts, vol. 95 (1981) 150317j.

(List continued on next page.)

*Primary Examiner*—Richard L. Raymond
*Attorney, Agent, or Firm*—Finnegan, Henderson, Farabow, Garrett and Dunner

[57] ABSTRACT

Process for preparing mono-, bi- and tricyclic amino acids, intermediates of this process, and a process for preparing same.

The invention relates to a process for preparing compounds of the formula I

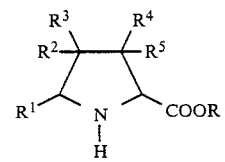

in which
R stands for hydrogen, alkyl or aralkyl and $R^1$ to $R^5$ are identical or different radicals, (substituted) alkyl, cycloalkyl or (substituted) aryl or in which the pairs of radicals $R^1$ and $R^2$, $R^2$ and $R^3$, and $R^4$ and $R^5$ together with the carbon atom(s) supporting them form a mono- or bicyclic ring system and the other radicals are hydrogen, by treating a compound of the formula II

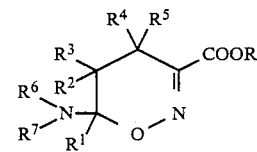

in which
R and $R^1$ to $R^5$ have the abovementioned meaning and $R^6$ and $R^7$ denote alkyl or aralkyl or together with the nitrogen atom supporting them form a heterocycle which can additionally contain an oxygen atom, with a reducing agent.

5 Claims, No Drawings

OTHER PUBLICATIONS

Gilchrist et al., Chemical Abstracts, vol. 92 (1980) 180643t.
J. Chem. Soc. Chem. Comm., 1089 (1979).
Leonard et al., J. Am. Chem. Soc., 77, 439 (1955).
Leonard et al., J. Am. Chem. Soc., 78, 3457 (1956).
Leonard et al., J. Am. Chem. Soc., 78, 3463 (1956).
Leonard et al., J. Am. Chem. Soc., 81, 5627 (1959).
Koelsch et al., J. Org. Chem., 26, 1104 (1961).
Griot et al., Helv. Chim. Acta, 42, 121 (1959).
Bonnett et al., J. Chem. Soc., 2087 (1959).
Battersby et al., J. Chem. Soc., 4333 (1958).
Rosenblatt et al., The Chemistry of Functional Groups, Supplement F: The Chemistry of Amino, Nitroso and Nitro Compounds and their Derivatives, Part II, S. Patai, ed., Wiley & Sons: New York 1982, pp. 1100–1104.
L. W. Haynes, Enamines, A. G. Cook, ed., Marcel Decker, Inc.: 1969, pp. 68–79, 261–269, 413.
Fieser & Fieser, Reagents for Organic Synthesis, vol. 1, pp. 644–651 (1967).
Boehme et al., Iminium Salts in Organic Chemistry, Part I (E. C. Taylor, ed.), Wiley & Sons: New York, 1976, p. 143.
S. Dayagi et al., The Chemistry of Functional Groups, the Chemistry of the Carbon-Nitrogen Double Bond, S. Patai, ed., Wiley & Sons: New York, 1970, p. 119.
W. Greenlee et al., J. Med. Chem., 28, 434–442 (1985).
K. Ogawa et al., J. Chem. Soc., Perkin Trans. I. 3031–3035 (1982).
R. Bacon and D. Stewart, J. Chem. Soc. (C), 1384–1387 (1966).
R. Bacon et al., J. Chem. Soc. (C), 1388–1389 (1966).
Patchett et al., Nature, 288, 280–283 (1980).
Booth et al., Chemistry and Industry, 466–467 (1956).
Booth et al., J. Chem. Soc., Part I, 1050–1054 (1959).
Murakoshi et al., Chemical Abstracts, 61, 9465(e)(1964).
Cushman et al., Fed. Proc., 38 (13), 2778–2782 (1979).
Houben-Weyl, Methoden der Organischen Chemie, 7(2b), 1403–1404 (1976).
Katritskaya, Dzh. Lagorskaya Khimia Geterosikl. Soedin., Moskow 1963, pp. 155–158.
Anderson, Jr. et al., J. Org. Chem., 43(1), 54–57 (1978).
Bertho et al., "Synthesen in der 2-Azabicyclo[0.3.-3]-octan-Reihe", Chemische Berichte, 92(7), 2218–2235 (1959).
Farkas et al., J. Org. Chem., 22, 1261–1263 (1957).
Taylor et al., J. Org. Chem. 38(16), 2817–2821 (1973).
Taylor et al., Heterocycles, 25, 343–345 (1987).
English Language Translation of Mitzlaff et al., Liebig's Ann. Chem., 1713–1733 (1978).
Chem. Berichte 86: 1524–1528 (1953).
Quarterly Reviews 25: 323–341 (1971)
Chem. Abst. 49/1955/3009c.
Nakanishi et al., Chem. Lett., (7), 869–872 (1981).

INTERMEDIATES FOR PREPARING MONO-, BI- AND TRICYCLIC AMINO ACIDS

This is a division of Ser. No. 122,380, filed 11-19-87, now U.S. Pat. No. 4,849,524.

Proline derivatives of the formula I are known from the literature. A process for their preparation is described EP-A-132,580. Surprisingly, there has now been found a process for preparing proline derivatives which is distinguished in particular by being simple to carry out.

The invention relates to a process for preparing compounds of the formula I

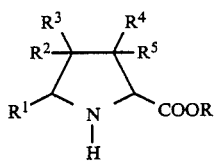

in which
R stands for hydrogen, $(C_1-C_6)$-alkyl or $(C_7-C_9)$-aralkyl, and
$R^1$ to $R^5$ are identical or different and independently of one another denote hydrogen, $(C_1-C_8)$-alkyl, $(C_3-C_9)$-cycloalkyl, $(C_3-C_9)$-cycloalkyl-$(C_1-C_4)$-alkyl, $(C_5-C_9)$-cycloalkenyl-$(C_1-C_4)$-alkyl, $(C_6-C_{12})$-aryl-$(C_1-C_4)$-alkyl or $(C_6-C_{12})$-aryl, where the two lastmentioned substituents can each be mono-, di- or trisubstituted in the aryl moiety by $(C_1-C_4)$-alkyl, $(C_1-C_4)$-alkoxy, hydroxyl, halogen, nitro, methylenedioxy and/or cyano, or in which the pairs of radicals $R^1$ and $R^2$, $R^2$ and $R^3$, and $R^4$ and $R^5$ together with the carbon atom or two carbon atoms supporting them form a 4- to 10-membered saturated or unsaturated mono- or bicyclic carbocyclic ring system and the other radicals are hydrogen, which comprises treating a compound of the formula II

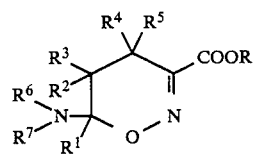

in which
R and $R^1$ to $R^5$ are identical or different and have the abovementioned meaning, and
$R^6$ and $R^7$ denote $(C_1-C_6)$-alkyl or $(C_7-C_9)$-aralkyl or $R^6$ and $R^7$ together with the nitrogen atom supporting them form a 5- to 10-membered heterocycle which can additionally contain an oxygen atom, with a reducing agent.

Suitable reducing agents are:
hydrogen in the presence of a catalyst such as palladium black, palladium on active carbon, platinum on active carbon, rhodium on active carbon, Raney nickel or Raney cobalt in a lower alcohol (such as $(C_1-C_4)$-alkanol) or a lower carboxylic acid (such as formic acid, acetic acid, propionic acid or butyric acid) with or without addition of a mineral acid such as, for example, hydrochloric acid, hydrobromic acid or sulfuric acid and also sodium borohydride, sodium cyanoborohydride, sulfited sodium borohydride ($NaBH_2S_3$), borane/dimethyl sulfide, borane/pyridine, borane/trimethylamine, sodium dithionite, sodium in a lower alcohol (such as $(C_1-C_4)$-alkanol), sodium amalgam or aluminum amalgam, but preferably reducing agents such as hydrogen in the presence of catalysts such as palladium black, palladium on active carbon, platinum on active carbon, rhodium on active carbon, Raney nickel or Raney cobalt.

The synthesis can be carried out between $-20°$ C. and the boiling point of the reaction mixture, preferably between 20° C. and 60° C. The $H_2$ pressure in the reaction is $1 \times 10^5$ to $2 \times 10^7$ N m$^{-2}$, preferably $1 \times 10^5$ to $5 \times 10^6$ N m$^{-2}$.

A preferred embodiment comprises preparing compounds of the formula I in which
R has the abovementioned meaning,
$R^1$ to $R^5$ are identical or different and independently of one another denote hydrogen, methyl, ethyl, propyl, isopropyl, tert.butyl, n-pentyl, cyclopentyl, cyclohexyl, cycloheptyl, cyclopentylmethyl, cyclopentylethyl, cyclohexylmethyl, phenyl, naphthyl, 4-methoxyphenyl, 4-fluorophenyl, 4-chlorophenyl, 3,4-dimethoxyphenyl, 3,4-methylenedioxyphenyl, 3,4-dichlorophenyl, p-tolyl, benzyl, 4-methoxybenzyl, 4-chlorobenzyl, phenethyl, 2-phenylpropyl or 1-phenylpropyl, or in which
the pairs of radicals $R^1$ and $R^2$, $R^2$ and $R^3$, and $R^4$ and $R^5$ form in the above-defined manner a cyclobutane, cyclopentane, cyclohexane, cycloheptane, cyclooctane, bicyclo[2.2.1]heptane or bicyclo[2.2.2]octane ring, the remaining radicals being hydrogen Particular preference is given to an embodiment which comprises preparing compounds of the formula I in which
R has the abovementioned meaning, but denotes in particular hydrogen, tert.butyl or benzyl, and in which one or two of the radicals $R^1$ to $R^5$ independently of each other denote methyl, ethyl, propyl, isopropyl, n-pentyl, cyclopentyl, cyclohexyl, phenyl, 4-methoxyphenyl, 4-fluorophenyl, benzyl, phenethyl or 4-methoxybenzyl and the others denote hydrogen, or
the pairs of radicals $R^1$ and $R^2$, and $R^2$ and $R^3$ together with the carbon atom or two carbon atoms supporting them form a cyclopentane, cyclohexane, cycloheptane, bicyclo[2.2.1]heptane or bicyclo[2.2.2]octane ring, the other radicals denoting hydrogen.

The process according to the invention produces the compounds of the formula I as mixtures of enantiomers or diastereoisomers or as pure diastereoisomers, depending on the way the process is carried out and the nature of the substituents $R^1$ to $R^5$. The resulting mixtures can be separated into their constituents by suitable methods known per se, such as fractional crystallization or chromatography in the case of diastereoisomers, or the formation of diastereoisomeric salts, if desired of suitable derivatives, in the case of enantiomeric mixtures.

The process according to the invention is very particularly advantageous for preparing the following compounds of the formula I.
ethyl cis-octahydro[1H]indole-2-exo-carboxylate
ethyl cis-octahydro[1H]indole-2-endo-carboxylate
ethyl trans-octahydro[1H]indole-2-α-carboxylate
ethyl trans-octahydro[1H]indole-2-β-carboxylate ethyl cis-octahydrocyclopenta[b]pyrrole-2-exo-carboxylate
ethyl cis-octahydrocyclopenta[b]pyrrole-2-endo-carboxylate
ethyl trans-octahydrocyclopenta[b]pyrrole-2-α-carboxylate
ethyl trans-octahydrocyclopenta[b]pyrrole-2-β-carboxylate
ethyl 2-azaspiro[4,5]decane-3-carboxylate
ethyl 2-azaspiro[4,4]nonane-3-carboxylate
ethyl spiro[bicyclo[2.2.2]octane-2,3'-pyrrolidine]-5-exo carboxylate
ethyl spiro[bicyclo[2.2.2]octane-2,3'-pyrrolidine]-5-endo carboxylate
ethyl spiro[bicyclo[2.2.1]heptane-2,3'-pyrrolidine]-5-exocarboxylate
ethyl cis-exo-3-azatricyclo[5.2.1.0$^{2,6}$]decane-4-exocarboxylate
ethyl cis-exo-3-azatricyclo[5.2.1.0$^{2,6}$]decane-4-endocarboxylate
ethyl cis-endo-3-azatricyclo[5.2.1.0$^{2,6}$]decane-4-endocarboxylate
ethyl cis-endo-3-azatricyclo[5.2.1.0$^{2,6}$]decane-4-exocarboxylate
ethyl cis-decahydrocyclohepta[b]pyrrole-2-exo-carboxylate
ethyl cis-decahydrocyclohepta[b]pyrrole-2-endo-carboxylate
ethyl trans-decahydrocyclohepta[b]pyrrole-2-α-carboxylate
ethyl trans-decahydrocyclohepta[b]pyrrole-2-β-carboxylate
ethyl 1-aza-spiro[4,5]decane-2-carboxylate
ethyl 1-aza-spiro[4,4]nonane-2-carboxylate
ethyl ester of 4,5-cis-diethylproline
ethyl ester of 4,5-cis-dimethylproline
ethyl ester of 5,5-dimethylproline
ethyl ester of 4,4-dimethylproline
ethyl ester of 4,4-diethylproline
ethyl ester of 3,3-dimethylproline
ethyl ester of 4,5-cis-diphenylproline
ethyl ester of 4-phenylproline and the corresponding free acids.

Compounds of the formula I in which R is $(C_1-C_6)$-alkyl or $(C_7-C_9)$-aralkyl can be converted in a manner known per se under hydrogenolytic, acid or basic conditions, for example with mineral acid such as hydrochloric acid, hydrobromic acid or sulfuric acid, at 0° to 150° C., preferably at 60° to 120° C., or with hydrogen in the presence of a transition metal catalyst, for example Raney nickel or palladium on active carbon, into compounds of the formula I in which R is hydrogen.

J. Chem. Soc. Chem. Commun 1979, 1089 describes the preparation of a compound of the formula II in which R is ethyl, $R^1$ and $R^2$ together form a $-[CH_2]_4$-chain, $R^3$ to $R^5$ stand for hydrogen and $R^6$ and $R^7$, together with the nitrogen atom supporting them, stand for a morpholine ring. Further reactions are not disclosed.

With the exception of this said compound, the compounds of the formula II are novel and likewise form part of the subject-matter of the invention The invention further relates to a process for preparing compounds of the formula II, which comprises reacting a compound of the formula III

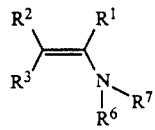

with a compound of the formula IV

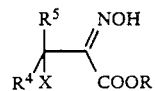

in which
R stands for hydrogen, $(C_1-C_6)$-alkyl or $(C_7-C_9)$-aralkyl,
$R^1$ to $R^5$ are identical or different and independently of one another denote hydrogen, $(C_1-C_8)$-alkyl, $(C_3-C_9)$-cycloalkyl, $(C_3-C_9)$-cycloalkyl-$(C_1-C_4)$-alkyl, $(C_5-C_9)$-cycloalkenyl-$(C_1-C_4)$-alkyl, $(C_6-C_{12})$-aryl-$(C_1-C_4)$-alkyl or $(C_6-C_{12})$-aryl, where the two last mentioned substituents can each be mono-, di- or trisubstituted in the aryl moiety by $(C_1-C_4)$-alkyl, $(C_1-C_4)$-alkoxy, hydroxyl, halogen, nitro, methylenedioxy and/or cyano, or in which pairs of radicals $R^1$ and $R^2$, $R^2$ and $R^3$, and $R^4$ and $R^5$ together with the carbon atom or two carbon atoms supporting them form a 4- to a 10-membered saturated or unsaturated mono- or bicyclic carbocyclic ring system and the other radicals are hydrogen,
$R^6$ and $R^7$ denote $(C_1-C_4)$-alkyl or $(C_7-C_9)$-aralkyl, or $R^6$ and $R^7$, together with the nitrogen atom supporting them, form a 5- to 10-membered heterocycle which can additionally contain an oxygen atom, and
X denotes chlorine or bromine.

The reaction is carried out in an aprotic organic solvent, preferably an ether such as, for example, diethyl ether, diisopropyl ether, tetrahydrofuran or dioxane or a chlorinated hydrocarbon such as, for example, dichloromethane or chloroform in the presence of a weak base such as, for example, sodium hydrogencarbonate, sodium carbonate, potassium carbonate or a trialkylamine or pyridine within a temperature range of $-40°$ C. to 100° C., preferably 0° C. to 50° C.

The compounds of the formula III are known from G. Cook, Enamines (Marcel Decker, New York and London, 1969) Compounds of the formula IV are obtained from compounds of the formula V

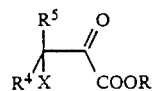

in which
R, $R^4$, $R^5$ and X are as defined above, by reaction with hydroxylamine, as described in J. Chem. Soc. Commun 1979, 1089.

The compounds of the formula I are useful intermediates in the preparation of pharmaceuticals, in particular in the preparation of inhibitors of angiotensin converting enzyme (ACE). Compounds of this type are known for example from EP-A-No. 50,800 or also form part of the subject-matter of German Patent Application P 31

51 690.4. These ACE-inhibitors are for example substituted acyl derivatives of the formula VI

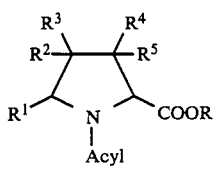    VI in which R, $R^1$ to $R^3$ are as defined above, $R^4$ and $R^5$ denote hydrogen, and acyl stands for example for a radical of the formula VII

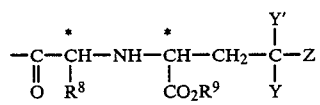    VII in which
$R^8$ denotes hydrogen, $(C_1-C_6)$-alkyl, which may be substituted by amino, $(C_1-C_4)$-acylamino or benzoylamino, $(C_2-C_6)$-alkenyl, $(C_5-C_9)$-cycloalkyl, $(C_5-C_9)$-cycloalkenyl, $(C_5-C_7)$-cycloalkyl-$(C_1-C_4)$-alkyl, aryl or partially hydrogenated aryl which can each be substituted by $(C_1-C_2)$-alkyl, $(C_1-C_2)$-alkoxy or halogen, aryl-$(C_1-C_4)$-alkyl whose aryl radical can be substituted as defined above, a mono- or bicyclic heterocyclic radical having 5 to 7 or 8 to 10 ring atoms, of which 1 to 2 ring atoms represent sulfur or oxygen atoms and/or of which 1 to 4 ring atoms represent nitrogen atoms, or denotes a side chain of an amino acid,
$R^9$ denotes hydrogen, $(C_1-C_6)$-alkyl, $(C_2-C_6)$-alkenyl or aryl-$(C_1-C_4)$-alkyl,
Y and Y' are hydrogen or together oxygen,
Z denotes $(C_1-C_6)$-alkyl, $(C_2-C_6)$-alkenyl, $(C_5-C_9)$-cycloalkyl, aryl which can be mono-, di- or trisubstituted by $(C_1-C_4)$-alkyl, $(C_1-C_4)$-alkoxy, hydroxyl, halogen, nitro, amino, $(C_1-C_4)$-alkylamino, di-$(C_1-C_4)$-alkylamino and/or methylenedioxy, or denotes indol-3-yl,
and their physiologically safe salts.

Compounds of the formula VI can be prepared for example by N-acylation of suitable esters of compounds of the formula I, such as, for example, benzyl or tert.-butyl esters with compounds of the formula acyl-OH, in which acyl is as defined above, and subsequent hydrogenolytic, acid or basic elimination of the ester groups.

The condensation of esters of the compounds of formula I with compounds of the formula acyl-OH is preferably effected by known methods of peptide chemistry. Particular preference is given to those methods which afford sufficient protection against racemization, such as, for example, the DCC/HOBt method or the alkanephosphonic anhydride method described in U.S. Pat. No. 4,331,592.

The compounds of the formula VI have an intensive and prolonged hypotensive action. They are readily absorbed after peroral administration and can be used for controlling blood hypertension of various origins and be employed by themselves or combined with other hypotensive, vasodilating or diuretically active compounds. They can be administered intravenously, subcutaneously or perorally, peroral administration being preferred The dosage in peroral administration is in general from 0.01 to 10 mg/kg per day. The dose can even be increased in serious cases, since toxic properties have hitherto not been observed. It is also possible to reduce the dose, which is advisable in particular when diuretics are administered at the same time. In the case of intravenous and subcutaneous administration, the individual dose should be between 0.1 and 250 µg/day.

The Examples which follow are intended to illustrate the invention without limiting it to the Examples described.

EXAMPLE 1

Ethyl cis-octahydro[1H]-indol-2-carboxylate (a) Ethyl 8a-morpholino-1-oxa-2-aza-1,4,4a,5,6,7,8,8a-octahydronaphthalene-3-carboxylate 5 g (30 mmol) of morpholinocyclohexene and 1.9 g (10 mmol) of ethyl 3-bromo-2-hydroxyiminopropionate are stirred at room temperature together with 2 g of potassium carbonate in 80 ml of dichloromethane for 4 hours. Filtration is followed by concentrating and chromatography over silica gel (eluant:ethyl acetate/cyclohexane 1:4). 2.1 g of a colorless oil are obtained $^1$H-NMR (CDCl$_3$): δ=4.3 (q,2H), 3.6 (t,4H), 2.8 (m, 2H), 2.6 (m,2H), 2.3 (m,2H), 1.4 (t,3H), 1.7-1.0 (m,9H) ppm.

(b) Ethyl cis-octahydro[1H]indol-2-carboxylate 2.1 g of the product of Example 1(a) are hydrogenated at 50° C. under atmospheric pressure in 60 ml of ethanol using 0.5 g of Raney nickel in the course of 4 hours. 1.3 g of ethyl cis-octahydro[1H]indol-2-carboxylate are obtained as a pale yellow oil after filtration and concentrating in vacuo.

EXAMPLE 2

Methyl cis-2-aza-bicyclo[3.3.0]octane-3-carboxylate (a) Methyl 1-morpholino-2-oxa-3-aza-bicyclo[4.3.0]non-3-ene-4-carboxylate 4.6 g (30 mmol) of morpholinocyclopentane are reacted with 1.75 g (10 mmol) of methyl 3-bromohydroxyiminopropionate by following the method of Example 1(a). 1.9 g of a colorless oil are obtained.

$^1$H-NMR (CDCl$_3$): δ=3.8 (s,3H), 3.6 (t,4H), 2.8 (m, 2H), 2.6 (m,2H), 2.3 (m,2H), 1.7-1.0 (m,3H) ppm.

(b) Methyl cis-2-aza-bicyclo[3.3.0]octane-3-carboxylate

The method of Example 1(b) is followed to convert 1.9 g of methyl 1-morpholino-2-oxa-3-aza-bicyclo[4.3.0]non-3-ene-4-carboxylate into 1.0 g of methyl cis-2-aza-bicyclo-[3.3.0]octane-3-carboxylate in the form of a pale yellow oil.

EXAMPLE 3

Ethyl spiro[bicyclo[2.2.2]octane-2,3'-pyrrolidine]-5'-carboxylate (a) Spiro[bicyclo[2.2.2]octane-2,5'-(6'-pyrrolidino)-4'H-5',6'-dihydro-1',2'-oxazine]

4.5 g (20 mmol) of 2-pyrrolidinomethylenebicyclo[2.2.2]-octane and 2.75 g (13 mmol) of ethyl 3-bromo-2-hydroxyiminopropionate are dissolved in 50 ml of dichloromethane. 5 g of sodium carbonate are then added and stirred in at 25° C. for 2 hours. Filtration is followed by concentrating. Chromatography over silica gel using ethyl acetate/cyclohexane (1:8) as an eluant gives 2.45 g of product. Melting point 116°–118° C. (n-hexane)

$^1$H-NMR (CDCl$_3$): δ=4.95+4.85 (2d,1H), 4.3 (2q,2H), 3.0 (m,2H), 2.7 (m,2H), 2.6+2.2 (AB system,2H), 1.9–1.4 (m,16H), 1.4 (t,3H) ppm.

(b) Ethyl spiro[bicyclo[2.2.2]octane-2,3'-pyrrolidine]-5'-carboxylate 2.4 g of the product of Example 3(a) are hydrogenated in 60 ml of ethanol using 0.4 g of Raney nickel by following the method described in Example 1(b). This gives 1.9 g of a pale yellow oil which contains the two diastereoisomers (S*,S* and S*,R*) in a ratio of 3:1. The isomers can be separated after acetylation with acetyl chloride/triethylamine in tetrahydrofuran Isomer 1 (S,S): 0.5 g, melting point 122° C.

$^1$H-NMR (CDCl$_3$): δ=4.4 (m,1H), 4.2 (q,2H), 3.9–3.1 (m,1H), 2.4–1.8 (m,1H), 2.1+1.95 (2s,3H), 1.7–1.3 (m,13H), 1.25 (t,3H) ppm.

Isomer 2 (S,R): 1.5 g, oil $^1$H-NMR (CDCl$_3$): δ=4.5–4.3 (m,1H), 4.3–4.1 (m,2H), 3.6–3.3 (m,2H), 2.4–1.8 (m,2H), 2.1+1.95 (2s,3H), 1.8–1.3 (m,12H), 1.3 (t,3H) ppm.

EXAMPLE 4

Ethyl ester of 4,4-pentamethyleneproline (a) 3-Ethoxycarbonyl-5,5-pentamethylene-6-pyrrolidino-4H-5,6-dihydro-1,2-oxazine 3.3 g (20 mmol) of pyrrolidinomethylenecyclohexane are reacted with 2.75 g (13 mmol) of ethyl 3-bromo-2-hydroxyiminopropionate by following the method of Example 3(a). 1.6 g of 3-ethoxycarbonyl-5,5-pentamethylene-6-pyrrolidino-4H-5,6-dihydro-1,2-oxazine are obtained in the form of an oil.

$^1$H-NMR (CDCl$_3$): δ=4.9 (s,1H), 4.3 (2q,2H), 3.0 (m,2H), 2.7 (m,2H), 2.6+2.2 (AB system,2H), 1.9–1.4 (m,14H), 1.4 (t,3H) ppm.

(b) Ethyl ester of 4,4-pentamethyleneproline 1.6 g of the product of Example 4(a) are hydrogenated using 0.2 g of Raney nickel by following the method given in Example 1(b). 0.9 g of a pale yellow oil is obtained.

$^1$H-NMR (CDCl$_3$): δ=4.2 (q,2H), 3.9 (m,1H), 3.4 (m,2H), 1.9–1.3 (m,12H), 1.25 (t,3H) ppm.

We claim:

1. A compound of the formula II

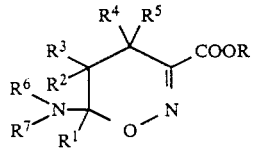

in which

R is hydrogen, (C$_1$–C$_6$)-alkyl or (C$_7$–C$_9$)-aralkyl,

R$^1$ to R$^5$ are identical or different and independently of one another denote hydrogen, (C$_1$–C$_8$)-alkyl, (C$_3$–C$_9$)-cycloalkyl, (C$_3$–C$_9$)-cycloalkyl-(C$_1$–C$_4$)-alkyl, (C$_5$–C$_9$)-cycloalkenyl-(C$_1$–C$_4$)-alkyl, (C$_6$–C$_{12}$)-aryl-(C$_1$–C$_4$)-alkyl or (C$_6$–C$_{12}$)-aryl, where the two last-mentioned substitutents can each be mono-, di- or trisubstituted in the aryl moiety by (C$_1$–C$_4$)-alkyl, (C$_1$–C$_4$)-alkoxy, hydroxyl, halogen, nitro, methylenedioxy and/or cyano, or in which the pairs of radicals R$^1$ and R$^2$, R$^2$ and R$^3$, and R$^4$ and R$^5$ together with the carbon atom or two carbon atoms supporting them form a 4- to 10-membered saturated or unsaturated mono- or bicyclic carbocyclic ring system and the other radicals are hydrogen, and R$^6$ and R$^7$ denote (C$_1$–C$_6$)-alkyl or (C$_7$–C$_9$)-aralkyl or R$^6$ and R$^7$ together with the nitrogen atom supporting them form a 5- to 10-membered heterocycle which can additionally contain an oxygen atom, with the proviso that simultaneously R does not stand for ethyl, R$^3$ to R$^5$ do not stand for hydrogen, R$^6$ and R$^7$ together with the nitrogen atom supporting them do not stand for a morpholine ring and (i) R$^2$ does not stand for methyl or ethyl in the case where R$^1$ is hydrogen, ethyl or phenyl and (ii) R$^1$ and R$^2$, together with the two carbon atoms supporting them, do not form a cyclopentane, cyclohexane or cycloheptane ring.

2. A compound of claim 1, wherein said compound is methyl 1-morpholino-2-oxa-3-aza-bicyclo[4.3.0]non-3-ene-4-carboxylate.

3. A compound of claim 1, wherein said compound is spiro[bicyclo[2.2.2]octane-2,5,'-(6'-pyrrolidino)-4'H-5',6,'-dihydro-1',2'-oxazine].

4. A compound of claim 1, wherein said compound is 3-ethoxycarbonyl-5,5-pentamethylene-6-pyrrolidino-4H-5,6-dihydro-1,2-oxazine.

5. A compound of the formula II

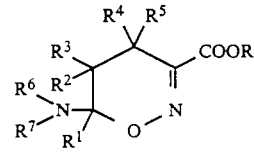

in which

R is hydrogen, (C$_1$–C$_6$)-alkyl or (C$_7$–C$_9$)-aralkyl,

R$^1$ to R$^5$ are identical or different and independently of one another denote hydrogen, (C$_1$–C$_8$)-alkyl (C$_3$–C$_9$)-cycloalkyl, (C$_3$–C$_9$)-cycloalkyl-(C$_1$–C$_4$)-alkyl, (C$_5$–C$_9$)-cycloalkenyl-(C$_1$–C$_4$)-alkyl, (C$_6$–C$_{12}$)-aryl-(C$_1$–C$_4$)-alkyl or (C$_6$–C$_{12}$)-aryl, where the two last-mentioned substituents can be mono-, di- or trisubstituted in the aryl moiety by (C$_1$–C$_4$)-alkyl, (C$_1$–C$_4$)-alkoxy, hydroxyl, halogen, nitro, methylenedioxy or cyano, or in which the pairs of radicals R$^1$ and R$^2$, R$^2$ and R$^3$, and R$^4$ and R$^5$ together with the carbon atom or two carbon atoms supporting them form a 4- to 10-membered saturated or unsautrated mono- or bicyclic carboxylic ring system and the other radicals are hydrogen, and R$^6$ and R$^7$ denote (C$_1$–C$_6$)-alkyl or (C$_7$–C$_9$)-aralkyl or R$^6$ and R$^7$ together with the nitrogen atom supporting them form a 5- to 10-membered heterocycle which can additionally contain an oxygen atom, with the proviso that simultaneously R does not stand for ethyl, R$^3$ to R$^5$ do not stand for hydrogen, R$^6$ and R$^7$ together with the nitrogen atom supporting them do not stand for a morpholine ring and (i) R$^2$ does not stand for methyl in case where R$^1$ is ethyl and (ii) R$^1$ and R$^2$, together with the two carbon atoms supporting them, do not form a cyclohexane ring.

* * * * *